US010952646B2

(12) United States Patent
Jayalath et al.

(10) Patent No.: US 10,952,646 B2
(45) Date of Patent: *Mar. 23, 2021

(54) WEARABLE PERFORMANCE MONITORING, ANALYSIS, AND FEEDBACK SYSTEMS AND METHODS

(71) Applicant: Mad Apparel, Inc., Redwood City, CA (US)

(72) Inventors: Dhananja Jayalath, Redwood City, CA (US); Christopher Wiebe, Redwood City, CA (US)

(73) Assignee: Mad Apparel, Inc., Redwood City, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 16/164,427

(22) Filed: Oct. 18, 2018

(65) Prior Publication Data

US 2019/0046086 A1    Feb. 14, 2019

Related U.S. Application Data

(63) Continuation of application No. 14/079,621, filed on Nov. 13, 2013, now Pat. No. 10,143,405.

(Continued)

(51) Int. Cl.
*A61B 5/11* (2006.01)
*A63B 24/00* (2006.01)
(Continued)

(52) U.S. Cl.
CPC .............. *A61B 5/1118* (2013.01); *A41D 1/04* (2013.01); *A61B 5/0004* (2013.01);
(Continued)

(58) Field of Classification Search
CPC ...... A61B 5/1118; A61B 5/6802–6807; A61B 5/6813; A61B 5/6814; A61B 5/6823;
(Continued)

(56) References Cited

U.S. PATENT DOCUMENTS 3,534,727 A    10/1970 Roman
3,973,099 A    8/1976 Morris
(Continued)

FOREIGN PATENT DOCUMENTS

WO    WO 2006/119345    11/2006

OTHER PUBLICATIONS

Merrit, C.R. et al., "Fabric-Based Active Electrode Design and Fabrication for Health Monitoring Clothing," IEEE Transactions on Information Technology in Biomedicine, Mar. 2009, pp. 274-280, vol. 13, No. 2.
(Continued)

*Primary Examiner* — David J. McCrosky
(74) *Attorney, Agent, or Firm* — Fenwick & West LLP (57) ABSTRACT

The present application relates generally to computer software, mobile electronics, wireless communication links, and wearable monitoring systems. More specifically, techniques, systems, sensors, circuitry, algorithms and methods for wearable monitoring devices and associated exercise apparatus are described. A garment borne sensor system may acquire data on a user's performance during exercise, for example. The data may be analyzed in real time and feedback may be provided to the user based on the analysis. Analysis may be used to alter behavior of the user and/or an apparatus the user is engaged with during an activity, such as exercise, conditioning, therapy, etc. A piece of exercise equipment may be instrumented and in communication with the sensor system or other system and may be controlled in real time to adjust its settings to affect the user during the exercise routine. Communication between the sensor system and other systems may be wireless.

22 Claims, 3 Drawing Sheets

Related U.S. Application Data (60) Provisional application No. 61/726,470, filed on Nov. 14, 2012, provisional application No. 61/726,474, filed on Nov. 14, 2012.

(51) Int. Cl.

| | | |
|---|---|---|
| *A61B 5/00* | (2006.01) | |
| *A61B 5/0488* | (2006.01) | |
| *A61B 5/0492* | (2006.01) | |
| *G09B 19/00* | (2006.01) | |
| *G16H 40/67* | (2018.01) | |
| *A61B 5/0402* | (2006.01) | |
| *A41D 1/04* | (2006.01) | |
| *A61B 5/0205* | (2006.01) | |
| *A61B 5/04* | (2006.01) | |

(52) U.S. Cl.
 CPC .......... *A61B 5/0015* (2013.01); *A61B 5/0022* (2013.01); *A61B 5/0402* (2013.01); *A61B 5/0488* (2013.01); *A61B 5/0492* (2013.01); *A61B 5/6804* (2013.01); *A61B 5/6805* (2013.01); *A61B 5/6841* (2013.01); *G09B 19/0038* (2013.01); *G16H 40/67* (2018.01); *A41D 2500/52* (2013.01); *A61B 5/02055* (2013.01); *A61B 5/04004* (2013.01); *A61B 2503/10* (2013.01); *A61B 2560/0223* (2013.01); *A61B 2562/0209* (2013.01); *A61B 2562/18* (2013.01); *A63B 2024/0009* (2013.01); *A63B 2024/0078* (2013.01)

(58) Field of Classification Search
 CPC ..... A61B 5/6828; A61B 5/6829; A61B 5/683; A61B 5/6831; A61B 5/02438; A61B 5/0205; A61B 5/02055; A61B 2503/10; G06F 19/3481; A63B 24/00–0006; A63B 24/0062; A63B 24/0075; A63B 24/0087; A63B 2024/0009–0015; A63B 24/0065–0071; A63B 24/0078; A63B 24/0081; A63B 24/009–0096
 See application file for complete search history.

(56) References Cited

U.S. PATENT DOCUMENTS

| | | |
|---|---|---|
| 4,170,225 A | 10/1979 | Criglar et al. |
| 4,400,341 A | 8/1983 | Sorensen |
| 4,729,377 A | 3/1988 | Granek et al. |
| 6,002,957 A | 12/1999 | Finneran |
| 6,350,129 B1 | 2/2002 | Gorlick |
| 6,381,482 B1 | 4/2002 | Jayaraman et al. |
| 6,755,795 B2 | 6/2004 | Mamaropoulos et al. |
| 6,970,731 B1 | 11/2005 | Jayaraman et al. |
| 6,978,684 B2 | 12/2005 | Nurse |
| 7,152,470 B2 | 12/2006 | Impio et al. |
| 7,173,437 B2 | 2/2007 | Hervieux et al. |
| 7,474,910 B2 | 1/2009 | Hassonjee et al. |
| 7,559,902 B2 | 7/2009 | Ting et al. |
| 7,602,301 B1 | 10/2009 | Stirling et al. |
| 7,783,334 B2 | 8/2010 | Nam et al. |
| 7,821,407 B2 | 10/2010 | Shears et al. |
| 7,825,815 B2 | 11/2010 | Shears et al. |
| 7,978,081 B2 | 7/2011 | Shears et al. |
| 8,006,633 B2 | 8/2011 | Bennett et al. |
| 8,032,199 B2 | 10/2011 | Linti et al. |
| 8,082,762 B2 | 12/2011 | Burr |
| 8,146,171 B2 | 4/2012 | Chung et al. |
| 8,214,007 B2 | 7/2012 | Baker et al. |
| 8,267,701 B2 | 9/2012 | Beaman et al. |
| 8,280,503 B2 | 10/2012 | Linderman |
| 8,475,371 B2 | 7/2013 | Derchak et al. |
| 8,560,044 B2 | 10/2013 | Kurzweil et al. |
| 8,750,959 B2 | 6/2014 | Lindberg et al. |
| 8,798,708 B2 | 8/2014 | Tremblay |
| 8,818,478 B2 | 8/2014 | Scheffler et al. |
| 8,821,305 B2 | 9/2014 | Cusey et al. |
| 8,909,318 B2 | 12/2014 | Nordstrom |
| 2003/0212319 A1 | 11/2003 | Magill |
| 2004/0187184 A1 | 9/2004 | Rubin et al. |
| 2004/0254624 A1 | 12/2004 | Johnson |
| 2005/0177059 A1 | 8/2005 | Koivumaa et al. |
| 2006/0264730 A1 | 11/2006 | Stivoric et al. |
| 2007/0038057 A1 | 2/2007 | Nam et al. |
| 2008/0092341 A1 | 4/2008 | Ahmadshahi |
| 2008/0096726 A1 | 4/2008 | Riley et al. |
| 2009/0012408 A1 | 1/2009 | Nagata et al. |
| 2009/0024017 A1 | 1/2009 | Ruffini et al. |
| 2010/0041974 A1 | 2/2010 | Ting et al. |
| 2010/0117837 A1 | 5/2010 | Stirling et al. |
| 2010/0185398 A1 | 7/2010 | Berns et al. |
| 2010/0204616 A1 | 8/2010 | Shears et al. |
| 2010/0234715 A1 | 9/2010 | Shin et al. |
| 2010/0251454 A1 | 10/2010 | Kiernan |
| 2010/0259407 A1 | 10/2010 | Tilvis et al. |
| 2010/0324405 A1 | 12/2010 | Niemi et al. |
| 2011/0257546 A1 | 10/2011 | Gozzini et al. |
| 2011/0288605 A1 | 11/2011 | Kaib et al. |
| 2012/0068759 A1 | 3/2012 | Clark et al. |
| 2012/0165645 A1 | 6/2012 | Russell et al. |
| 2012/0208156 A1 | 8/2012 | Rocklin |
| 2012/0330126 A1 | 12/2012 | Hoppe et al. |
| 2013/0077263 A1 | 3/2013 | Oleson et al. |
| 2013/0137943 A1 | 5/2013 | Rodrigues |
| 2013/0137956 A1 | 5/2013 | Okuda et al. |
| 2013/0172722 A1 | 7/2013 | Ninane et al. |
| 2013/0192071 A1 | 8/2013 | Esposito et al. |
| 2013/0324368 A1 | 12/2013 | Aragones et al. |
| 2014/0070949 A1 | 3/2014 | Chen |
| 2014/0097944 A1 | 4/2014 | Fastert et al. |
| 2014/0172134 A1 | 6/2014 | Meschter |
| 2014/0180023 A1 | 6/2014 | Stivoric et al. |
| 2014/0189928 A1 | 7/2014 | Oleson et al. |
| 2014/0275888 A1 | 9/2014 | Wegerich et al. |
| 2014/0296651 A1 | 10/2014 | Stone |
| 2014/0352023 A1 | 12/2014 | Mordecai et al. |
| 2015/0047091 A1 | 2/2015 | Fournier et al. |
| 2015/0148619 A1 | 5/2015 | Berg et al. |
| 2015/0181692 A1 | 6/2015 | Jezewski et al. |

OTHER PUBLICATIONS

United States Office Action, U.S. Appl. No. 15/331,869, dated Jan. 14, 2019, 10 pages.
United States Office Action, U.S. Appl. No. 14/079,621, dated Nov. 6, 2017, 10 pages.
United States Office Action, U.S. Appl. No. 14/079,621, dated May 12, 2017, 11 pages.
United States Advisory Action, U.S. Appl. No. 14/079,621, dated Jun. 30, 2016, 4 pages.
United States Office Action, U.S. Appl. No. 14/079,621, dated Mar. 16, 2016, 16 pages.
United States Office Action, U.S. Appl. No. 14/079,621, dated Oct. 19, 2015, 15 pages.

WEARABLE PERFORMANCE MONITORING, ANALYSIS, AND FEEDBACK SYSTEMS AND METHODS

CROSS-REFERENCE TO RELATED APPLICATIONS

This application is a continuation of U.S. patent application Ser. No. 14/079,621, filed on Nov. 13, 2013, now U.S. Pat. No. 10,143,405, which claims priority to U.S. Provisional Patent Application No. 61/726,470, filed on Nov. 14, 2012, and to U.S. Provisional Patent Application No. 61/726,474, filed on Nov. 14, 2012, all of which are herein incorporated by reference in their entirety for all purposes.

FIELD

The present application relates generally to computer software, mobile electronics, wireless communication links, and wearable monitoring systems. More specifically, techniques, systems, sensors, circuitry, algorithms and methods for wearable monitoring devices and associated exercise apparatus are described.

BACKGROUND

Human bio-potentials have long been measured in clinical settings for heath and/or performance monitoring purposes. For example, the heart rate (HR) of a human test subject may be monitored in a health clinic or other health care venue using an electrocardiogram (ECG) system. In a typical electrocardiography test, a plurality of ECG electrodes may be adhesively attached to the skin of the human test subject in order to record information pertaining to the heart. The measured bio-potential information indicative of the heart functions may typically be recorded on ECG graph paper or stored in computer memory for later analysis.

In general, conventional ECG electrodes may be formed of a conductive gel embedded in an adhesive pad onto which a cable is coupled. Examples include an adhesive conductive hydrogel formed over a conductive rigid sensor to which the cable is coupled or otherwise attached. ECG electrodes may be adhesively attached to different locations on the skin of the human test subject to obtain heart-related information from different angles (e.g., left arm, right arm, left leg, etc.). The electrical signals obtained by the ECG electrodes may then be interpreted by a knowledgeable expert to obtain certain information pertaining to the heart functions (e.g., heart rate (HR), heart rhythm, etc.) as well as to detect symptoms of pathological conditions (e.g., hypocalcaemia, coronary ischemia, hypokalemia, myocardial infarction, etc.), for example.

There are some disadvantages to conventional gel-based electrodes. Gel-based and/or adhesive-based electrodes may be unsuitable for long-term monitoring applications. For example, gel-based and/or adhesive-based electrodes tend to dry out over time and thus tend to be one-time-use-only devices. Furthermore, gel-based and/or adhesive-based electrodes, such as those employing Silver-Silver chloride (Ag/AgCl) electrodes, may cause skin irritation to some human subjects, especially if those electrodes are used over a long period of time. Moreover, the expertise and/or dexterity required to adhesively attach the gel-based and/or adhesive-based electrodes at various specific locations on the body often requires the use of an expert human assistant. The need for such expert involvement may be inconvenient and/or awkward for the user, and may drive up the cost associated with long-term monitoring.

The same issues may also render gel-based and/or adhesive-based electrodes unsuitable for use in the consumer market. For example, in addition to the aforementioned bio-compatibility issue, consumers may be resistant to purchasing, using, and discarding one-time-use gel-based and/or adhesive-based electrodes due to cost concerns and/or environmental impact concerns. As mentioned above, the attachment of gel-based and/or adhesive-based electrodes at specific locations on the skin may be intimidating and time-consuming to an average consumer and may require a level of expertise and/or dexterity that an unaided consumer typically may not possess.

Conventional dry electrodes have been proposed as an alternative electrode that addresses the aforementioned shortcomings of gel-based and/or adhesive-based electrodes. In that dry electrodes may be based on conductive rubber rather than gel or adhesive, dry electrodes typically do not dry out like typical gel-based and/or adhesive-based electrodes. Skin compatibility and reusability may be greatly enhanced by using dry electrodes.

Conventional dry electrodes and associated amplifying circuitry have been incorporated into textiles (e.g., garments), resulting in textile-based monitoring clothing. See, for example, "Fabric-Based Active Electrode Design And Fabrication For Health Monitoring Clothing" by Carey R. Merrit and H. Troy Nagle (IEEE Transactions On Information Technology In Biomedicine, Vol. 13, No. 2, March 2009). Textile-based monitoring garments based on textile monitoring fabric have further been manufactured and made commercially available by different manufacturers.

One of the seismic shifts in consumer electronic trends in recent years has been the increase in processing (e.g., multiple core and/or faster processors) and communication capabilities (e.g., WiFi, Bluetooth, NFC, Cellular, 2G, 3G, 4G, and 5G) of smart personal communication devices (SPCDs) and the ubiquitous nature of the Internet in everyday life. More importantly, SPCDs have been widely adopted by consumers and are ubiquitous in the consumer market. For example, SPCDs incorporating both cellular telephony capability and computer-like data processing and communication capabilities have been widely adopted by consumers for communication, work, Internet surfing, health, personal fitness, and entertainment (e.g., movie watching, gaming, streaming media, social and professional networking, etc.). Examples of such SPCDs include smart phones and tablets incorporating operating systems such as iOS™ (available from Apple, Inc. of Cupertino, Calif.), Android™ (available from Google, Inc. of Mountain View, Calif.), Windows™ (available from Microsoft Corporation of Redmond, Wash.), and the like. Well-known contemporary brands of smart phones and tablets include, for example, iPhone™, iPad™, Samsung Galaxy™, Motorola Droid™ BlackBerry™, etc. These SPCDs are now ubiquitous and possess powerful communication and processing capabilities. The popularity and utility of SPCD's have resulted in them being carried by their users at all times or at least being kept nearby and ready for use.

The ubiquitous nature of the Internet, the pervasiveness of wireless communications networks, and the widespread adoption of SPCDs and their constant access and use by consumers has provided an opportunity to create comprehensive textile-based monitoring garment systems that may provide a level of capability and user-friendliness unavailable with the above mentioned conventional textile-based monitoring garment solutions.

Therefore, there is a need for improved electrodes, materials, ease of use, reduced costs, and features in textile-based monitoring garment systems.

BRIEF DESCRIPTION OF THE DRAWINGS

Various embodiments or examples ("examples") are disclosed in the following detailed description and the accompanying drawings.

It is to be understood that, in the drawings, like reference numerals designate like structural elements. Also, it is understood that the drawings are not necessarily to scale.

DETAILED DESCRIPTION

Various embodiments or examples may be implemented in numerous ways, including as a system, a process, an apparatus, a user interface, or a series of program instructions disposed in a non-transitory computer readable medium such as a computer readable storage medium (e.g., RAM, SRAM, DRAM, ROM, Cache, Register, Flash, SSD, HHD, Volatile memory, Non-volatile memory, Optical media, Magnetic media, etc.) or a computer network where the program instructions are sent over optical, electronic, or wireless communication links. In general, operations of disclosed processes may be performed in an arbitrary order, unless otherwise provided in the claims.

A detailed description of one or more examples is provided below along with accompanying figures of the drawings. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

In some examples, the described techniques may be implemented as a computer program or application ("application") or as a plug-in, module, or subcomponent of another application. The described techniques may be implemented as software, hardware, firmware, circuitry, Integrated Circuit (IC), ASIC, FPGA, or a combination thereof. If implemented as software, the described techniques may be implemented using various types of programming, development, scripting, or formatting languages, frameworks, syntax, applications, protocols, objects, compilers, or techniques, including but not limited to ASP, ASP.net, .Net framework, Ruby, Ruby on Rails, C, Objective C, C++, C #, Adobe® Integrated Runtime™ (Adobe® AIR™), ActionScript™, Flex™ Lingo™, Java™, Javascript™, Ajax, Perl, COBOL, Fortran, ADA, XML, MXML, HTML, DHTML, XHTML, HTTP, XMPP, PHP, an objected oriented language, and others. Design, publishing, and other types of applications such as Dreamweaver®, Shockwave®, Flash®, Drupal and Fireworks® may also be used to implement the described techniques. Database management systems (i.e., "DBMS"), search facilities and platforms, web crawlers (i.e., computer programs that automatically or semi-automatically visit, index, archive or copy content from, various websites (hereafter referred to as "crawlers")), and other features may be implemented using various types of proprietary or open source technologies, including MySQL, Oracle (from Oracle of Redwood Shores, Calif.), Solr and Nutch from The Apache Software Foundation of Forest Hill, Md., among others and without limitation. The described techniques may be varied and are not limited to the examples or descriptions provided.

In some examples, a form-fitting sensor garment may include at least one sensor (e.g., a bio-potential sensor) and associated processing and communications electronics. In other examples, the one or more sensors may be washable sensors that may be borne or otherwise coupled with a garment and configured to be unaffected and/or undamaged by washing or otherwise cleaning or maintaining the garment. One or more form-fitting sensor garments may be made to be conformal to any part of the human body as desired. In other examples, one or more form-fitting sensor garments may be made to be conformal to any part of a structure, such as on the body of a non-human species (e.g., animals, mammals, pets, avian, livestock, equine, sea creatures, denizens of the deep, etc.), for example. Stretchable, compressive and form-fitting fabric made of natural or preferably synthetic fibers (e.g., nylon, lycra, polyester, spandex, or other suitable fibers and blends thereof) may be configured to exert a biasing force on the sensors, which are built-in to the form-fitting sensor garment, to bias (e.g., urge into contact) the washable sensors against the skin to maintain good electrical and/or mechanical contact and to reduce motion artifacts that may be caused if there is relative motion between the skin and the sensor(s) (e.g., the sensors and/or skin sliding against each other along their mutual contacting surfaces).

Bioimpedance sensors may include but are not limited to ECG sensors, electromyography (EMG) sensors, respiration, galvanic skin response (GSR), or others. Other types of sensors may also be incorporated into the form-fitting sensor garment. These auxiliary sensors may include but are not limited to accelerometers (single or multi-axis), vibration sensors, GPS sensors, magnetometers, location sensors, galvanic skin response (GSR), bioimpedance, gyroscopes, respiration, heart rate, bend-angle measurement sensors and/or flex angle measurement sensors (e.g., to measure joint angle or joint angles), etc. These sensors may be incorporated in a permanent manner into the fabric of the form-fitting sensor garment itself or in a detachable manner and/or in pockets or under or on top of flaps if desired. Preferably, most or all the sensors, including the non-detachable sensors, are constructed and built such that they can withstand repeated washing and drying cycles typical of wearable clothing.

The present application describes implementation of a combination of a multitude of sensors including, but not limited to electromyography (EMG), electrocardiograph (ECG), galvanic skin response (GSR), temperature, acceleration, bend angle, etc. The use of multiple sensors provides a level of insight that is not available by measuring only a single metric such as heart rate (HR) or motion based on accelerometers or other types of motion sensors (e.g., a gyroscope), as is currently available.

Conventional products do not enable washable electromyography sensors and associated electrodes attached to a form-fitting garment in the manners disclosed in one or more embodiments herein. The various combinations of embodiments disclosed herein that include electromyography sensors, dry electrodes, analysis and feedback methods, normalization and/or communication scope have not existed in conventional sensor garments.

In one or more embodiments, sensors may be incorporated into fabric or other material in a semi-permanent manner (using, e.g., loop-and-hook fasteners or other detachable fastening means) to allow re-positioning of the sensors.

In one or more embodiments, processing electronics may be configured to acquire the sensed signals from the sensors and/or to amplify/filter the sensed signals from the sensors may be incorporated into the form-fitting sensor garment in a permanent or detachable manner. In some examples, the sensors are detachably mounted to the garment to for a purpose including but not limited to repairs, replacement, upgrades, updates to software, sensor calibration, power source maintenance, to install on a different garment, to exchange for another sensor or type of sensor, just to name a few. Further, in one or more embodiments, processing electronics may be configured to perform data processing/analysis on the sensed data which are derived from the sensed signals from the electrodes). Processing electronics may also be incorporated into the form-fitting sensor garment in a permanent or detachable manner. The processing electronics may also include one or more radios for wireless communication with external devices and/or other systems in the garment. For example, the processing electronics may comprise a system-on-chip (SoC) that may include one or more radios (e.g., BT, WiFi, NFC, etc.). As described herein, the term sensor may include one or more electrodes and associated sensor electronics (e.g., in a processor or other circuitry) electrically coupled with the electrodes and configured to acquire signals from the electrodes and to process the acquired signals in an analog domain, a digital domain or both. A sensor may comprise electrodes and associated sensor electronics integrated into a common structure such as an electrode pad, or may comprise electrodes and sensor electronics that are disposed remotely from one another, such as electrodes coupled to a remotely positioned processor (e.g., positioned at another location in the garment) or other circuitry using an electrically conductive structure such as a conductive trace, wire, cable, or the like, for example.

In one or more embodiments, communication electronics may be configured to transmit and/or receive information wirelessly and may be incorporated into the form-fitting sensor garment in a permanent or detachable manner. In one or more embodiments, a network of signal conductors may be configured to facilitate communication among the sensors and/or communication electronics and/or processing electronics may be permanently incorporated into the fabric of the form-fitting sensor garment.

To provide power to the processing electronics and/or communication electronics and/or sensors, a power source such as one or more batteries (which may be rechargeable by various means or may be one-time-use, disposable batteries) may be incorporated into the form-fitting sensor garment in a permanent or detachable manner. If the electronics and/or power source are/is non-detachable, it is preferable that these components are constructed such that they can withstand repeated washing and drying cycles typical of wearable clothing.

In the following discussion, electromyography sensors are described only as an example to facilitate discussion. It should be understood, however, that the present application contemplates that other types of sensor may be implemented additionally and/or alternatively to the electromyography sensors discussed in connection with the examples herein. In one or more embodiments, multiple washable electromyography (WE) sensors may be used to measure muscle activity at different sites on the human body. The WE sensors may be configured to measure muscle activity associated with different muscles to measure muscle exertion intensity. When groups of muscles are measured together, more complex analysis and feedback may be performed and made available to the user (e.g., wirelessly via an application (APP) running on a smartphone, tablet, pad, or the like).

In the following discussion, concepts of the present application will be described using athletics as well as strength and conditioning as an example application. The benefit of a garment that includes a multitude of WE sensors and specifically the ability to monitor multiple muscles, without requiring conventional adhesive based and manually placed alternatives may be utilized for other applications. The end use application in which the sensors and garment described herein may be used does not change the form or function of the concepts described in the present application. For example, applied to ergonomics the ability to critique form and posture discussed herein can be used to train proper procedures in a manufacturing environment, work environment, and athletic endeavors, just to name a few. Critiquing posture may provide injury prevention in the workplace in the same way as in an athletic training setting. As another example, in that the present application builds on clinical methods and provides a more user-friendly experience, the present application may be applied for use in self-guided rehabilitation and injury prevention training.

One example of the complex analysis and feedback possible using multiple WE sensors comprises a bench-press exercise routine because the bench press routine exercises a plurality of different muscles in the human body. By detecting muscle exertion intensity associated with each of the plurality of muscles, information such as whether the human subject is using the proper form, whether a muscle is injured and compensation by one or more other muscles is taking place, whether the user is exercising with the optimal number of repetition and intensity, whether the full range of motion is involved, etc., may be acquired (e.g., from signals from multiple sensors) and provided as instant feedback to the user and/or to adjust the exercise the equipment (e.g., in real time) to optimize the exercise session. Other types of sensors (such as one or more of the aforementioned bend-angle measurement sensors, GSR, HR, temperature, and accelerometers, for example) may also provide information to enrich the analysis and feedback regarding the example bench-press routine.

In one or more embodiments, the set of WE sensors may be permanently incorporated into the fabric of the form-fitting sensor garment. In one or more embodiments, the form-fitting sensor garment may come in various sizes to accommodate various body sizes (e.g., similar to the sizing system currently used with exercise or casual clothing). In one or more embodiments, it is recognized that the difference in skin condition and/or subcutaneous fat content from human subject to human subject may give rise to data acquisition error if left uncorrected. For example, raw sensor signals acquired from a user with a higher body fat percentage may differ from raw sensor signals acquired from a leaner user even though they both may weigh the same and may fit into the same size garment. The subcutaneous fat layer between muscle tissue and skin surface may attenuate an electromyography signal resulting in different acquired amplitudes for different body types. The output from the sensor may be calibrated, in one or more embodiments, to improve analysis and feedback accuracy.

In one or more embodiments, the number of electrodes/sensors that are built into the fabric exceeds the number actually required to obtain the necessary muscle activity data. Logic and/or heuristics may be employed to select the sensors that provide the best signals for the group of muscles of interest. This is particularly advantageous since the human subject may position the garment slightly differently at different times or in different work-out sessions. Further, the optimal measurement sites for one user may be different from the optimal measurement sites for other users. Prior to work out, intelligent logics and/or algorithms may be employed to select the optimal group of sensors on the form-fitting sensor garment to use for actual monitoring and analysis. As another example, the user may be guided to engage in a training or a teaching routine to allow the textile-based MAFS to properly recognize and select the optimal group of sensors on the form-fitting sensor garment to use in the actual monitoring and analysis. Signals from sensors that are not selected may be ignored or given less weight or may be employed in other ways, for example.

In one or more embodiments, all sensor data from all available sensors may be collected and/or stored (e.g., in memory), and analysis may be performed only on the subset of sensors that are relevant and/or deemed to generate most optimal signals for analysis. In other embodiments, only the relevant subset of sensor data may be collected and/or stored and/or analyzed. One or more of the collecting, the storing, or the analyzing may occur internally (e.g., on one or more processors or controllers in the garment), externally (e.g., in an external device such as the SPCD or other wireless device) or both.

In one or more embodiments, the design of the garment and geometry of the electrodes may be configured to account for variations in user body types and resulting alignment concerns. Intuitive features may be added to the garment to ensure proper alignment. These may include, but are not limited to, visible lines, markers and cut-outs for thumb, elbow, etc. For example, alignment marks or markers including but not limited to visible lines may provide a guide where the user only needs to ensure the line is straight for proper alignment. The electrode geometry may be designed to account for different muscle sizes. In one example, increasing a dimension of the electrode orthogonal to the muscle fiber direction may accommodate varying fiber radii and resulting muscle volume. In other examples, the garment may include designed structures configured to urge and/or force the user to correctly position the garment and its sensors with proper and/or orientation with respect to the muscles or other portions of the user's body to be sensed. For example, a shirt-like garment may include a cut-out portion for one or more body parts such as one for an elbow and another for a thumb and/or one or more fingers. The user aligning the elbow cut-out with the elbow of his/her arm and the fingers and/or thumb with their respective cut-outs may be used to ensure at least approximately accurate alignment of sensors in an arm portion of the shirt-like garment with the muscles in the arm that are to be sensed by the sensors disposed in the arm portion of the shirt-like garment. As another example, a pant-like garment may include for each leg, a heel loop and a knee cut-out configured to align sensors in a leg portion of the pant-like garment with the intended muscles in the user's legs. Other types of design structures may be configured into a garment were appropriate and may be used in conjunction with one or more alignment marks included with the garment. The above are non-limiting examples of designed structures and the present application is not limited to the above examples.

In one or more embodiments, the user may be given real-time feedback based not only on the sensed bio-signals, but also on analysis of the sensor outputs (e.g., acquired signals from electrodes and/or other auxiliary sensors). For example, pattern recognition algorithms may be employed to detect whether the muscle exertion data from a group of muscles indicates that the user is engaging in incorrect form or in a non-optimal workout. For example, exercises targeting the biceps brachii are meant to isolate exertion of that muscle from the rest of the body. A less efficient workout occurs when the user generates momentum using the shoulder and/or lower back. Identifying activity in these momentum-influencing muscles can determine incorrect form. Accelerometer or bend-angle data may be incorporated to complement the aforementioned. The feedback is preferably made in visual or audible form to allow the user to easily understand muscle activity and how to improve and/or correct a workout routine. In this manner, virtual coaching may be accomplished in real time to coach the user over the course of the workout.

In one or more embodiments, the form-fitting sensor garment may be part of a textile-based human MAF system. Processing and communication electronics on the form-fitting sensor garment may allow for data exchange (e.g., via a wireless communications link) with the exercise equipment, the smart personal communication device (SPCD), the feedback device and/or the Internet (e.g., computers implemented remotely and available via the Internet). In one or more embodiments, user-friendly techniques for pairing and communicating among the various components of the textile-based human MAF system are disclosed.

The features and advantages of various embodiments of the textile-based human MAF system may be better understood with reference to the figures and discussions that follow.

Figure 1A:
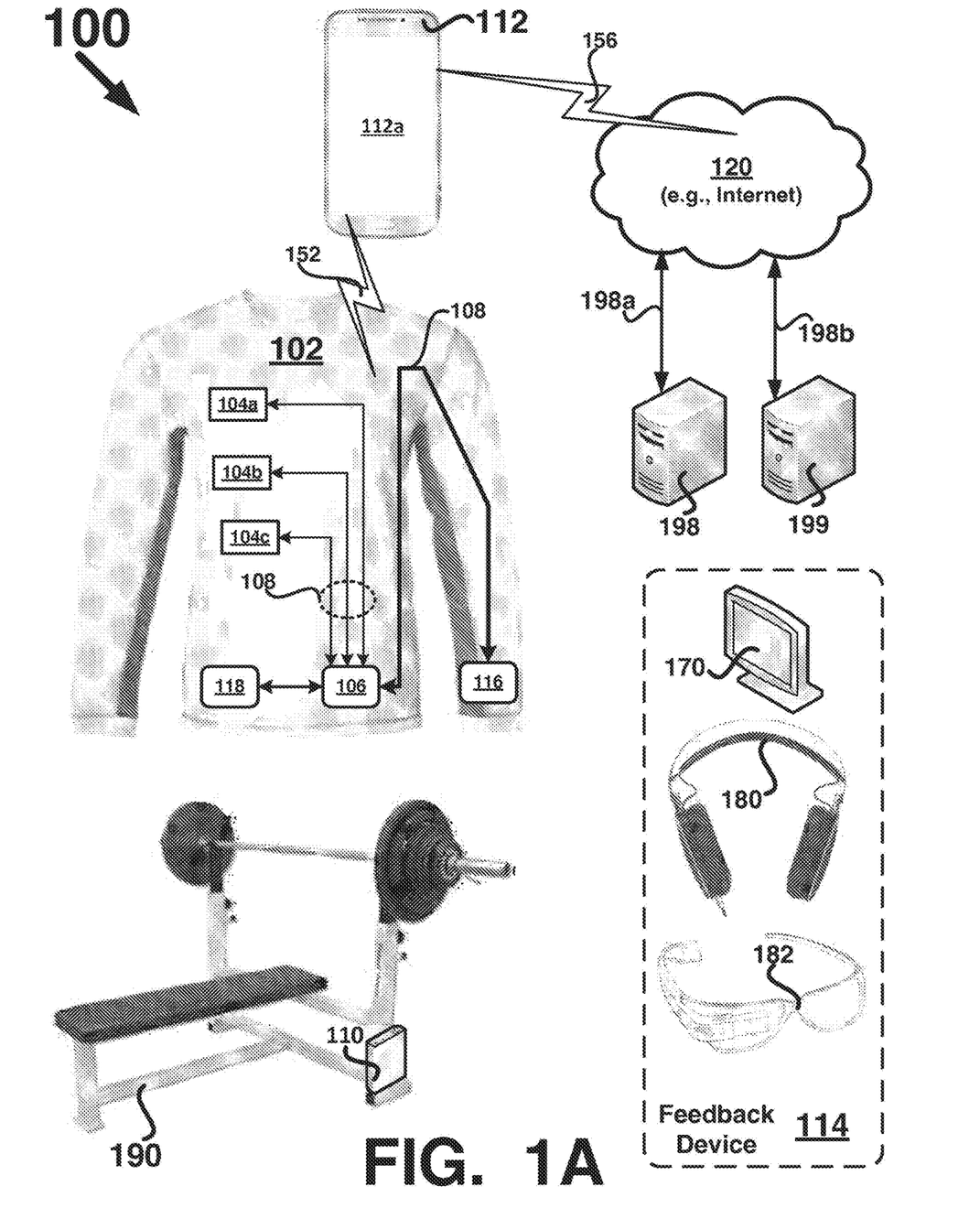
FIG. 1A depicted an example of a simplified representation of various components of a textile-based human monitoring, analysis, and feedback (MAF) system.

FIG. 1A depicted an example of a simplified representation of various components of a textile-based human monitoring, analysis, and feedback (MAF) system 100.

With reference to FIG. 1A, there is depicted a form-fitting sensor garment 102, representing a compressive, stretchable, and form-fitting garment to be worn by a human subject (not shown). Although form-fitting sensor garment 102 is shown to be a shirt, it can take any other garment form factor including but not limited to shorts, pants, elbow pad, knee pad, undergarment, neck wrap, glove, and the like, etc. A plurality of sensors 104A, 104B, and 104C are depicted as being disposed at various positions on the fabric of form-fitting sensor garment 102. As described above, a pair of electrodes and associated electronics may form a sensor, which may receive as inputs a potential difference generated on the human skin due to ions flowing in muscle fibers as a result of muscle activity. The associated electronics of the sensor may include filtering and impedance transferring. Although only three sensors (104A-104C) are depicted, it should be understood that there is no limit to the number and different types of sensors that may be employed and more or fewer sensors may be implemented than are depicted in the example of FIG. 1A.

In an embodiment, the electrodes of the sensor may be disposed on the inside of the garment such that they make electrical contact with the skin generally at locations where muscles of interest are expected to be located adjacently when the form-fitting sensor garment 102 is worn. As mentioned above, in an embodiment, redundant sensors may be incorporated into the garment to take into account the fact that the human subject may not wear the garment exactly the same way every time or different human subjects may be built differently. Also as mentioned, intelligent logic may then determine, from all available sensors, the optimal for use in monitoring performance in connection with a particular exercise routine. Moreover, as described above, designed structures, alignment marks, markers or other visual indicia may be positioned on and/or woven into, or otherwise integrated with the form-fitting sensor garment 102 to aid the user in correct placement of the sensors when putting on (e.g., donning garment 102) the form-fitting sensor garment 102. The designed structures, alignment marks or other visual indicia may be configured or otherwise designed to include an esthetic element, a logo, an icon, a fashion design, a distinctive pattern, or a color scheme, for example. In other examples, the alignment marks or other visual indicia may serve a variety of purposes, such as in machine/computer vision analysis of the motion of the human subject's body during an activity being monitored by the sensors 104A-104C, where a machine/computer vision apparatus may use the alignment marks or other visual indicia to track body motion or motion of a portion of the body the alignment marks or other visual indicia are positioned on. Analysis of sensor data from the sensors as well as data from the vision analysis (e.g., in real-time) may be used for a variety of purposes including but not limited to coaching the user, physical therapy, choreography, stunts and/or special effects in movies and/or TV, athletic pursuits, competitions, or other endeavors that involve motion of the body. Other sensors such as gyroscopes, magnetometers, accelerometers, temperature, GSR, HR, bioimpedance, etc., may be used in some combination in conjunction with sensors 104A-104C and the machine/computer vision apparatus.

Typically, electrodes of sensors 104A-104C may be a solid conductive material bonded or woven or a conductive resin (e.g., polymers, silicone, neoprene, thermoplastics, etc.) applied through a screening, printing or gluing process, or combination thereof, in either a permanent or detachable manner, to the fabric or to another conductive substrate attached to the fabric of the form-fitting sensor garment 102. The electrodes may be formed from a flexible PCB substrate (e.g., Kapton or other laminates) that may be bonded to the garment 102. Thus, unlike the conventional electrodes described above, the user does not have to manually attach the sensor to different specific locations on the skin in the manner required for conventional physiological monitoring apparatus. In the example herein, sensors 104A-104C may be washable electromyography sensors although it should be understood, as mentioned, that other types of sensors may well be alternatively or additionally employed. Preferably, sensors 104A-104C are constructed such that they may withstand repeated wash-and-dry cycles typical of wearable clothing. In other examples, sensors 104A-104C are constructed such that they may withstand repeated wash-and-hang-dry cycles typical of wearable clothing. Form-fitting sensor garment 102 may be made from materials, circuitry, structures or the like that may be amendable to any number of wash cycles (e.g., in a washing machine or hand washing) and/or drying cycles (e.g., in a gas or electric dryer). Form-fitting sensor garment 102 may be made from materials, circuitry, structures or the like that may be amendable to dry-cleaning processes and the chemicals used in dry-cleaning processes. However, in some applications it may be preferable to hang-dry (e.g., air dry) garment 102, to preserve an appearance of the material (e.g., fabrics, colors, dyes, etc.) used for the garment 102, to prevent dryer lint or the like from gathering on the garment 102, and to prevent damage to the garment 102, its electronics, fabrics, sensors, or the like due to inadvertently drying the garment 102 at too high a temperature. In some applications garment 102 may be configured for machine drying, air drying, or both. Actual washing and/or drying instructions and/or processes for the garment 102 will be application dependent and are not limited to the examples described herein.

A controller 106 may be coupled with sensors 104A-104C via a network of flexible signal conductors 108 (which may be electrically conductive or optical). In one embodiment, sensors 104A-104C may communicate with controller 106 via a wired (e.g., hard wired) interface. In another embodiment, sensors 104A-104C may communicate with controller 106 via a wireless interface that may user a variety of wireless protocols including but not limited to NFC, Bluetooth, any variety of 802.x, just to name a few. Preferably, signal conductors 108 may be constructed such that they can also withstand repeated wash-and-dry cycles or wash and hang-dry cycles that typical of wearable clothing. Bonded insulated conductors, such as Kapton and laminate based printed circuit boards, wire, cable, coaxial conductors, shielded conductors, flexible printed circuits (FPC), flat flexible cable (FFC), electrically conductive threads, or silk-screened/printed electrically conductive resins are examples of technologies that may be used to implement signal conductors 108. In some examples, sensors 104A-104C may communicate with controller 106 using a combination of wired and wireless communications links. Controller 106 may comprise one or more controllers or one or more processors. In some examples controller 106 may alternatively be referred to as a processor or processor 106.

Typically, controller 106 may include communication electronics (e.g., one or more radios for a wireless communications link) to permit form-fitting sensor garment 102 to communicate (e.g., wireless data) with one or more of exercise equipment communication device 110, smart personal communication device (SPCD) 112 (e.g., a smart phone, tablet, or pad), feedback device 114 (if such feedback device is other than SPCD 112), or the Internet 120 via an appropriate router/access point arrangement, such as a wireless network (e.g., Bluetooth (BT), BT Low Energy, NFC, WiFi, any variety of IEEE 802.x, etc.). The electronics for implementing controller 106 may be permanently attached to the fabric of form-fitting garment (in which case controller 106 may be constructed such that it can withstand repeated wash-and-dry and/or wash and hang dry cycles typical of wearable clothing) or may be detachable from the garment 102 prior to washing/drying the garment 102.

Figure 1B:
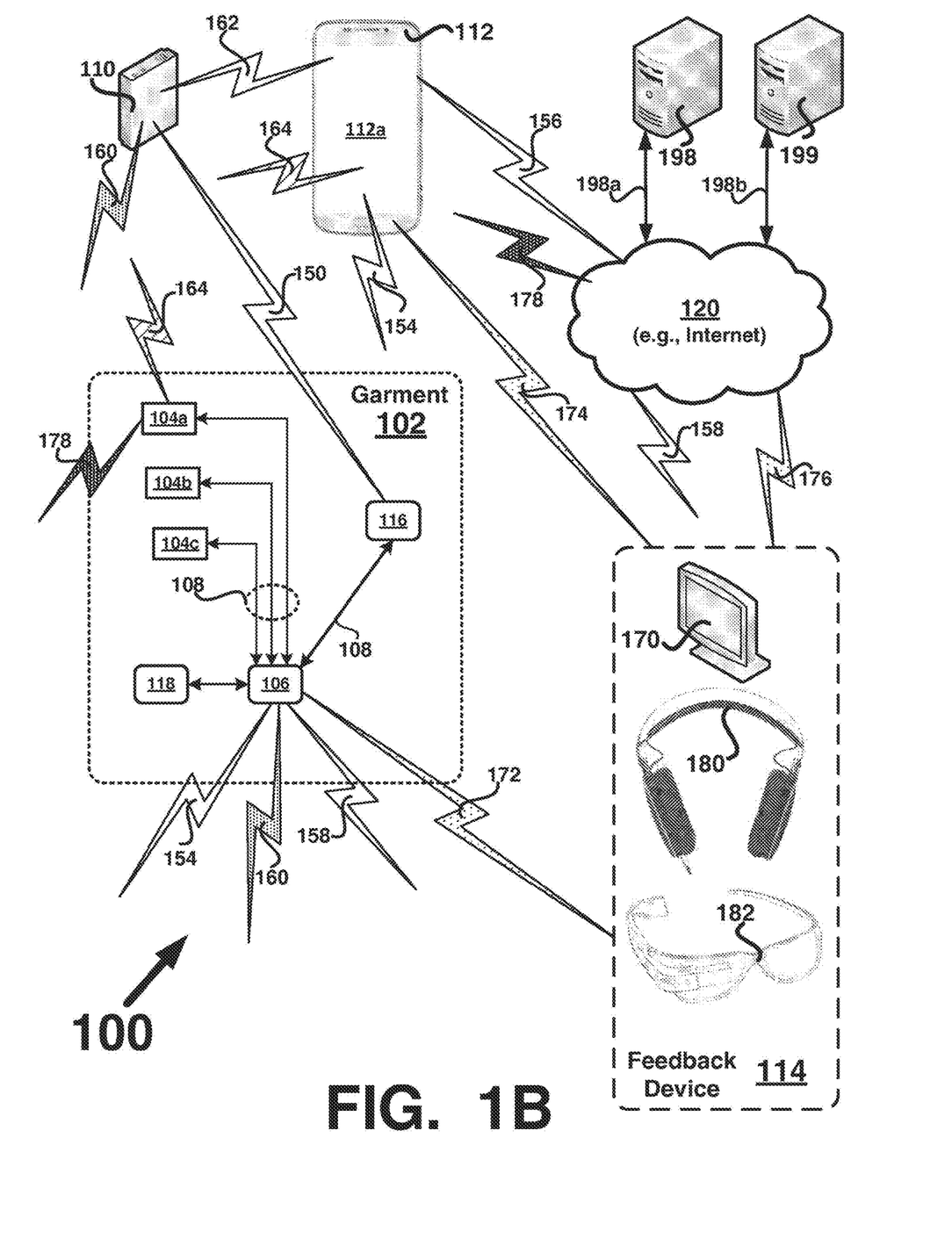
FIG. 1B one example of various components of the textile-based human MAF system depicted in FIG. 1A.

Controller 106 may also include processing electronics for performing some or all required signal processing on the sensed signals acquired from electrodes in sensors 104A-104C. In one or more embodiments, such signal processing (e.g., amplifying or filtering) may be performed locally in one or more of the sensors 104A-104C, at the controller 106, or both, for example. Controller 106 may also include signal processing for performing data analysis and feedback data generation. In one or more embodiments, such data analysis and feedback data generation may be performed at one or more of controller 106, SPCD 112, feedback device 114 (if such feedback device is other than SPCD 112), or the Internet 120. Therefore, signal processing for performing data analysis and feedback data generation may occur solely in the garment 102 and its associated electronic circuitry, external to garment 102, or both where some portion of the processing is done in the garment and other portions are done external to the garment 102 using processors and resources of external devices and/or systems. Controller 106 may include one or more processors, multi-core processors, one or more digital signal processors (DSP), one or more micro-processors (µP), one or more micro-controllers (µf), one or more application specific integrated circuits (ASIC), one or more field programmable gate arrays (FPGA), one or more analog-to-digital converters (ADC), one or more digital-to-analog converters (DAC), a system on chip (SoC), one or more operational amplifiers, custom logic, programmable logic, analog circuitry, mixed analog and digital circuitry, or the like, just to name a few. Garment 102 may include one or more radios configured to transmit, receive, or both, radio frequency (RF) signals for one or more wireless communications links as described above in reference to FIGS. 1A-1B. A plurality of radios may communicate using a plurality of wireless protocols and the plurality of wireless protocols may be different protocols.

FIG. 1A also depicts an example of an optional equipment detector (ED) 116, representing a communication device (e.g., a wireless device) for obtaining information from exercise equipment communicating device 110. Typically, it is contemplated that each piece of exercise equipment in a gym or other exercise facility may be equipped with its own exercise equipment communicating device 110 (e.g., a wired or wireless communications link). For example, exercise equipment communicating devices 110 may be implemented using RFID (Radio Frequency ID) devices, NFC (Near Field Communication) devices, some form of tag implemented in computer readable code such as QR (Quick Response) code or bar code, or even communication electronics that broadcast (e.g., wirelessly, either on its own or in response to an inquiry) information regarding the exercise equipment (e.g., 190) or the types of exercises that may be performed on the exercise equipment. The information from the exercise equipment communicating devices 110 may be read by equipment detector 116 in order to acquire the aforementioned information regarding the exercise equipment or the types of exercises that may be performed on the exercise equipment.

Electrical power for equipment detector (ED) 116, sensors 104A-104C, and controller 106 may be provided by a battery pack 118, which may be attached to form-fitting sensor garment 102 in a permanent or detachable manner. Battery pack 118 may represent a one-time-use, disposable battery or may represent a rechargeable battery pack (e.g., Lithium-Ion, Nickel Metal Hydride, or the like) to be recharged for use via a charging port (e.g., a micro USB connector) implemented with battery pack 118 or on form-fitting sensor garment 102 or via a wireless charging technology such as inductive charging. The battery pack 118 (rechargeable or otherwise) may be configured to be replaceable (e.g., by the user) in the event the battery fails or to swap out a battery with low charge or no charge, with a freshly charged battery, for example. Battery pack 118 may be configured to accept batteries with different amp-hour capacities to provide sufficient duration of operation of garment 102 and its associated electronics, such as 1500 mAh, 3000 mAh, etc. Battery pack 118 may be configured to endure several wash cycles, dry cycles or both. Alternatively, battery pack 118 may be configured to be removable from garment 102 when the garment 102 is to be washed and/or dried.

Figure 2:
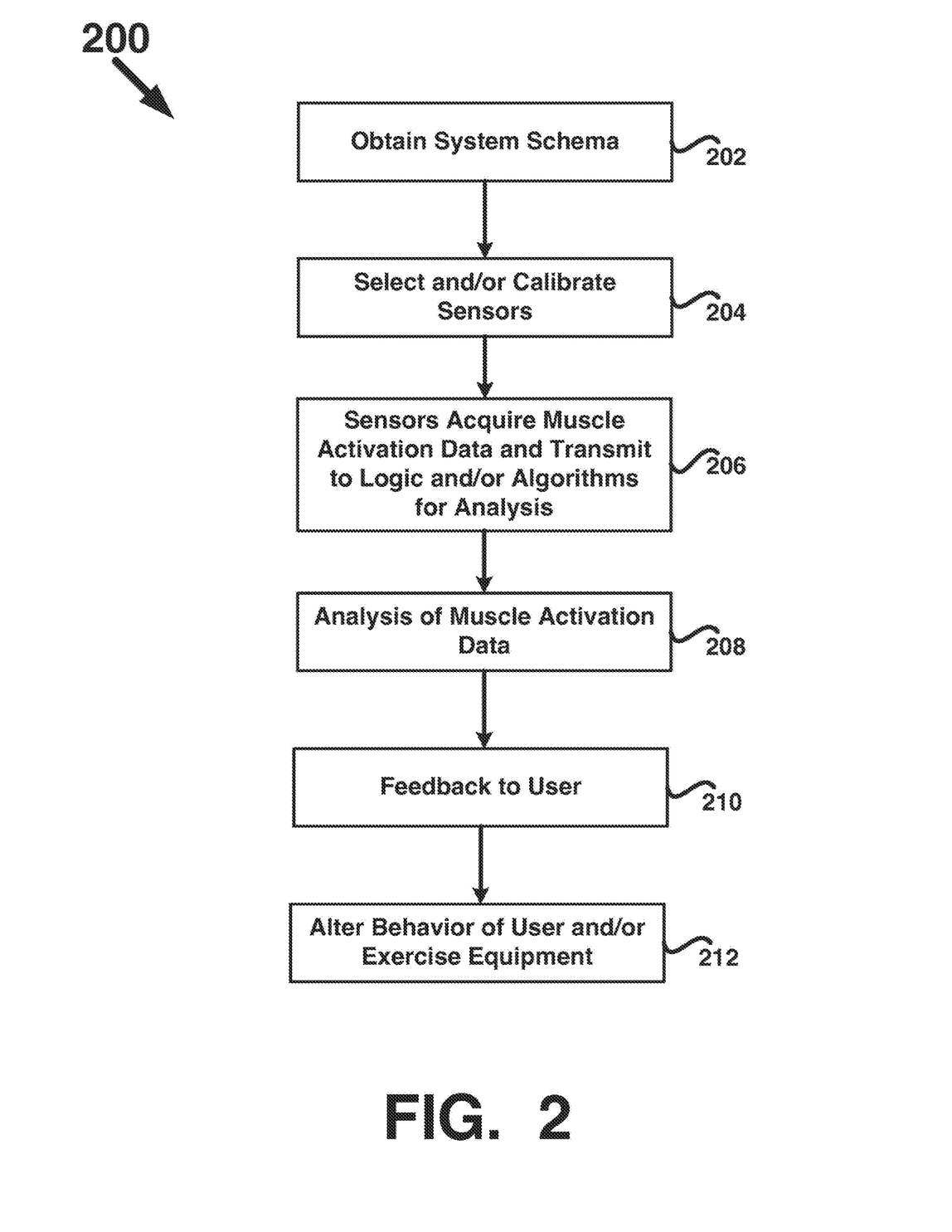
FIG. 2 depicts an example use scenario for the textile-based human MAF system depicted in FIG. 1A.

FIG. 2 depicts an example use scenario 200 for the textile-based human MAF system 100 depicted in FIG. 1A. The stages depicted in FIG. 2 may be better understood when reviewed together with FIG. 1B which depicts one example of various components of the textile-based human MAF system 100 depicted in FIG. 1A. Components depicted in FIG. 1B may have similar reference numbers to components depicted in FIG. 1A and may be intended to represent similar components.

Referring again to FIG. 2, at a stage 202, a system schema is obtained. As the term is employed herein, the system schema may represent the reference muscle exertion data associated with a given exercise. For example, a bicep curl exercise may be represented by a system schema that specifies the level of exertion that should be experienced by the bicep muscle (e.g., fairly high) and lower back muscle (e.g., fairly low). The system schema may include one or more other schemas including but not limited to a user schema, a workout schema, and an environmental schema, just to name a few. System schema may be a combination of workout and/or exercise parameters, user specific parameters (e.g., BMI, percent body fat, weight, amount of bodily hair, etc.).

In accordance with a highly advantageous aspect of the present application, a system schema associated with a particular exercise may be automatically obtained in a user-friendly manner (e.g., wirelessly) without requiring data entry by the human subject. In an embodiment, equipment detector (ED) 116 may be brought into range (e.g., wireless range or near-field wireless range for NFC) or enabled to read information from or communicate with exercise equipment communicating device 110, which is affixed to the exercise equipment (e.g., a bench press machine 190 or other piece of equipment) or associated therewith.

Information (e.g., data) obtained from exercise equipment communicating device 110 may be as simple as a code that identifies the exercise equipment (e.g., "bench press equipment") or the exercise to be performed (e.g., "bench press"). This information may be relayed (e.g., wirelessly) from ED 116 to controller 106 (e.g., see paths 150/152 in FIG. 1B) so that controller 106 may decode the information to obtain the system schema at the stage 202.

Alternatively, the information acquired by ED 116 may be relayed from ED 116 to controller 106 and then to SPCD 112 (e.g., see paths 150/152/154 of FIG. 1B) so that SPCD 112 may decode the information to obtain the system schema. Alternatively, the information may be further relayed from SPCD 112 to the Internet 120 (e.g., see paths 150/152/154/156) or from controller 106 to the Internet 120 and bypassing SPCD 120 (e.g., see paths 150/152/158). One or more computers 198 and 199 may be implemented remotely and may communicate (198a, 198b) via Internet 120 may then decode the relayed information to obtain the system schema and to send the information back.

Alternatively, the information from the exercise equipment communicating device 110 may be obtained directly by controller 106 and may bypass ED 116 (e.g., see path 160) or by SPCD 112 and may bypass both ED 116 and controller 106 (e.g., see path 162). For example, controller 106 or SPCD 112 may directly read or sense the information from exercise equipment communicating device 110 in one or more embodiments. After direct acquisition by controller 106 or by SPCD 112, the information from exercise equipment communicating device 110 may be processed in any of the manners discussed above (e.g., by controller 106, by SPCD 112, or by Internet 120 via any other paths depicted in FIG. 1B) to obtain the system schema at the stage 202. In some examples Internet 120 may be a resource such as a web site, web page, cloud storage, cloud computing, a server farm, network attached storage (NAS), RAID storage, or other resource that may provide compute engines (e.g., 198, 199) and/or data storage. Computers 198 and 199 may be directly coupled with data storage (not shown) or in communication with external data storage (e.g., Internet 120) (not shown). Examples of data storage include but are not limited to hard disc drives (HDD), solid state drives (SSD), RAID, NAS, Optical Disc, Flash memory, just to name a few.

In one or more examples, the information provided from exercise equipment communicating device 110 to ED 116 or controller 106 or SPCD 112 (e.g., depending on implementation) may be as complete as the entire system schema itself. In this example, no decoding is necessary to obtain the system schema at the stage 202.

In an additional example, SPCD 112 may retrieve the system schema at the stage 202 from a locally stored and pre-determined workout regimen or from the Internet 120 based on a user profile, for example. In this example, information from communicating device 110 may not be required provided that the user follows the predetermined regimen as instructed using SPCD 112.

Referring again to FIG. 2, sensors 104A-104C may be selected and/or calibrated in preparation for monitoring at a stage 204. Sensor selection may be performed if the form-fitting sensor garment 102 has redundant sensors. Calibration may be performed to take into account effects including but not limited to different body fat percentages, BMI's, bodily hair, or other factors associated with different human subjects, for example.

At a stage 206, muscle activation data may be acquired by sensors 104A-104C (or other sensors) while the user performs the exercise and transmitted to logic for analysis. The muscle activation data may be communicated via signal conductors 108 (as mentioned in connection with FIG. 1A) to controller 106. Analysis may be performed at controller 106 if controller 106 is endowed with logic and/or algorithms (e.g., software and/or hardware and/or firmware) to perform the analysis (in which case controller 106 may have to access to the earlier discussed system schema at the stage 202 for analysis purpose). This is shown by a path for signal conductors 108 in FIG. 1B. Although all of the sensors 104A-104C are depicted directly coupled to a single controller 106, it should be understood that such coupling may be an actual/physical coupling or may be a logical coupling. For example, multiple controllers (e.g., multiple controllers 106) may cooperate to share the data processing task or to relay information from one or more sensors to the appropriate controller or controllers for further data processing.

Alternatively, the muscle activation data may be communicated from sensors 104A-104C to controller 106 and then may be relayed to SPCD 112 for analysis (in which case SPCD 112 may have access to the earlier discussed system schema at the stage 202 for analysis purpose). This is depicted by paths 108/154 in FIG. 1B.

At this point, a short description regarding wireless communication may be useful. Typically, wireless communication among components of textile-based human MAF system 100 may employ any suitable air interface, including for example Bluetooth™ (in its various implementations, including low power Bluetooth), ANT™, WiFi™, WiMAX™, infrared, cellular technology (such as for example GSM™, CDMAT™, 2G™, 3G™, 4G™, 5G™, LTE™, GPRS™), etc. The selection of the appropriate air interface for communication depends on the air interface availability in the devices and/or at the location, cost, convenience, and/or other factors.

Alternatively or additionally, the muscle activation data may be forwarded from SPCD 112 to Internet 120 (e.g., via path 164/156 or path 108/154/156) or from controller 106 to Internet 120 bypassing SPCD 120 (e.g., path 108/158) for analysis by one or more remotely implemented computers (e.g., 198, 199) through Internet 120.

Alternatively, the muscle activation data may be communicated from sensors 104A-104C directly to Internet 120 for analysis (in which case the sensors 104A-104C may be equipped with communication circuitry such as wireless communication circuitry, and computers (e.g., 198, 199) implemented via the Internet 120 may have access to the earlier discussed system schema at the stage 202 for analysis purpose). This is shown by example path 178 in FIG. 1B. Computers (e.g., 198, 199) may be in wired or wireless communication (198a, 198b) with the Internet 120.

In accordance with a particularly advantageous aspect of the present application, analysis may be performed not only on a single muscle, but on a plurality of muscles in accordance to the system schema at the stage 202. Analysis may be performed at one or more of the controller 106, the SPCD 112, the Internet 120, or any combination thereof, for example.

Analysis at a stage 208 may include, in one or more embodiments, comparing the exertion level of individual muscles (e.g., obtained from the muscle activation data from the sensors 104A-104C) with the reference exertion level of those muscles (e.g., obtained from the system schema at the stage 202). This analysis may reveal, for example, whether the human subject is performing the exercise at the appropriate intensity level (e.g., by looking at the intensity data from the sensors 104A-104C and comparing such information with corresponding information in the reference system schema at the stage 202). This analysis may also reveal, for example, whether the human subject is performing the exercise incorrectly. This may be the case if, for example, one muscle in the group of muscles under monitoring by the sensors 104A-104C is over-exerted or under-exerted. Other sensor data such as bend-angle sensor data or accelerometer sensor data may be used to improve the accuracy of the analysis at the stage 208.

Analysis at the stage 208 may include, alternatively or additionally, comparing the duration of the exertion of individual muscles (e.g., obtained from the muscle activation data from the sensors 104A-104C) with the reference exertion duration of those muscles (e.g., obtained from the system schema at the stage 202). Analysis may include, alternatively or additionally, comparing the number of exertion repetitions in a set (obtained from the muscle activation data from the sensors 104A-104C) with the reference exertion repetitions for those muscles (e.g., obtained from the system schema at the stage 202).

Analysis at the stage 208 may include, alternatively or additionally accumulating an activity score based on an electromyography signal. Such a score may be in different resolution forms such as the overall body or individual muscles. This allows the user to compare intensity level as measured through muscle exertion over time.

Analysis at the stage 208 may include, alternatively or additionally determining the number of repetitions and an approximation of the weight used. Such analysis may be determined by statistical analysis on saved user data or by comparing the user data against a larger data set of all active users stored in Internet 120 in FIG. 2. User data may be stored on one of controller 106, SPCD 112 or equipment 110.

Analysis at the stage 208 may include, alternatively or additionally updating a user profile and comparing against profiles of one or more other users. In one embodiment, user profile data may include a history of workout sessions including overall exertion as well as individually monitored muscles. In another embodiment, profile data may include goals set by the user and additionally or alternatively challenges from other users (e.g., to motivate the user). For example, the challenges may come from other persons or users who may be associated with a social network (e.g., Facebook®, Twitter®), professional network (e.g., LinkedIn®), or the like. Through social and/or professional networking of user profiles including historical workout data, motivation is increased by the competitive environment created. Additionally, challenges may be proposed by the system (e.g., controller 106 and/or other system in communication with controller 106). A combination of progressive challenges (e.g., a series of challenges, each with higher goals to be achieved) may lead the user to higher and higher levels as in a gaming scenario were gameificaiton of the challenges may comprise the user taking on progressive challenges against goals set by the user, the system, others, or by other competitors in the game, for example.

In accordance with a particularly advantageous aspect of the present application, a result of the analysis at the stage 208 may be immediately communicated to the user at a stage 210 via a display 112*a* of device 112 (e.g., a smartphone, table, pad, eyeglasses 182, etc.) or an auxiliary feedback device such as devices 114 substantially in real time (e.g., immediately after data acquisition and analysis is completed, factoring in real-world delays in data transmission and processing). Feedback at the stage 210 may, for example, include a representation of the body and visually depict the muscles being exerted, along with a color gradient or an overlay with relative exertion or other data depiction scheme to communicate the intensity level and/or duration and/or number of repetitions associated with each muscle. The feedback at the stage 210 may also include recommendations (e.g., "push more with the left arm" "slow down when lowering your arm") or warning (e.g., "do not swing while lifting") or other coaching information while the human subject is performing the exercise. The feedback at the stage 210 may be alternatively or additionally be in the form of audio feedback (e.g., on SPCD 112 or device 180), in one or more embodiments.

Additionally, feedback at the stage 210 may be stored on either the controller 106, the SPCD 112 or the Internet 120 for later viewing and/or audio playback. In one example, after completing a set or portion of a workout session the user may "playback" visual features including the body representation with muscle depiction. This allows the user to get feedback at a time that is convenient and not during a strenuous activity. Other features can be added to compare the "playback" with other users who may be a part of the system environment. For example using a professional athlete as a benchmark of comparison.

Feedback device 114 may be implemented by a built-in display 112*a* of SPCD 112 (e.g., a LCD, OLED, touch screen, etc.) by an external display 170, by audio playback device (such as headset 180, which may be in communication with controller 106, SPCD 112, external display 170 and/or Internet 120), or by digital eyewear (see 182 in FIG. 1A). Feedback device 114 may provide feedback information in either graphical, video, or audio format to the user.

For example, the analysis result at the stage 208 (e.g., as a type of feedback at the stage 210) may be displayed on the display screen 112*a* of SPCD 112 after analysis by SPCD 112. Alternatively, the analysis result may be displayed (e.g., using wireless communication if necessary) on the display screen 112*a* of SPCD 112 if analysis takes place elsewhere (e.g., communicated via path 154 if analysis is performed on controller 106 or via path 156 if analysis is performed via Internet 120). Alternatively or additionally, the analysis result may be displayed on an external display 170 (e.g., communicated via path 172 or path 154/174 if analysis is performed on controller 106 or communicated via path 156/174 or path 176 if analysis is performed by Internet 120).

Alternatively or additionally, the analysis result at the stage 208 may be displayed on digital eyeglasses (see 182 in FIG. 1A) instead of external display 170. Alternatively or additionally, the analysis result at the stage 208 may be converted to an audio format and played back using a headset 180 (e.g., a wireless headset, earpiece, headphones, or the like).

In accordance with a particularly advantageous aspect of the present application, the analysis result at the stage 208 may be employed to alter the behavior of the exercise equipment 190 in order to improve the exercise experience and/or exercise efficacy for the human user at a stage 212. For example, if the user is perceived to employ bad form while exercising at the maximum intensity level, the resistance level of a stationary bicycle or the incline angle of a treadmill or the resistance level of a resistance exercise equipment may be automatically reduced (e.g., in real time, using a motor or transducer operating under the command of controller 106 or SPCD 112) in order to help improve the exercise form of the user. Contrarily, if the analysis at the stage 208 reveals that the user can rapidly perform the exercise without much muscle strain, the resistance level of a stationary bicycle or the incline angle of a treadmill or the resistance level of a resistance exercise equipment may be changed (e.g., in real time) in order to present a more meaningful or beneficial exercise to the human subject.

In accordance with a particularly advantageous aspect of the present application, the system schema at the stage 202 may be individualized and/or customized using data such as the user's profile/objective data (e.g., BMI, weight, height, training experience, past exercise session data) or the user's subjective input (e.g., training goal, desired exertion level/duration/number of repetitions/number of sets). Objective data could be simplified by asking the user to identify with visual representations (e.g., using a GUI on display 112*a*) of different body types to reduce the amount of manual input required. In this manner, the human subject's workout session may be individualized and/or customized when the muscle activation data is compared against the individualized and/or customized system schema at the stage 202.

In one or more embodiments, the system schema at the stage 202 may also be customized using social and/or professional network input. For example, recommendations from coaches or challenges from other workout partners may be employed to change the system schema at the stage 202 in order to provide the human subject with a more optimal workout session. Customization using social and/or professional network input may be accomplished in real-time (e.g., to optimize the present workout session) or may occur post workout in preparation for future workout sessions where the recommendations may be acted on to optimize the workout session.

In accordance with one or more embodiments, form-fitting sensor garment 102 (or more specifically controller 106 of form-fitting sensor garment 102) may automatically pair with SPCD 112. Pairing, in the context of the present invention, may pertain to the association of a specific device with another specific device to facilitate wireless data communication and/or wireless data security/confidentiality. Likewise, form-fitting sensor garment 102 (or more specifically controller 106 of form-fitting sensor garment 102) may automatically pair (e.g., BT paring) with exercise equipment 190 (or more specifically with exercise equipment communication device 110 thereof). Likewise, SPCD 112 may automatically pair with exercise equipment 190 (or more specifically with exercise equipment communication device 110).

In one or more embodiments, form-fitting sensor garment 102 (or more specifically controller 106 of form-fitting sensor garment 102) may intelligently pair with SPCD 112 to reduce power consumption (e.g., from battery pack 118). In an example of intelligent pairing, the communication apparatus would be turned off during periods of inactivity, such as when the user is resting. When controller 106, through algorithmic implementation, detects the commencing of activity the communicating apparatus would be turned on and pairing completed. Likewise, form-fitting sensor garment 102 (or more specifically controller 106 of form-fitting sensor garment 102) may intelligently pair with exercise equipment 190 (or more specifically with exercise equipment communication device 110 thereof) to reduce power consumption. Likewise, SPCD 112 may intelligently pair with exercise equipment 190 (or more specifically with exercise equipment communication device 110) to extend battery life. In other embodiments, processor 106 may scan for sensor activity from one or more of the sensors (e.g., 104A-104C) and if no sensor activity is detected, then processor 106 may switch to a low power mode of operation (e.g., to conserve battery power). Upon detecting sensor activity, processor 106 may exit the low power mode, analyze the detected sensor activity (e.g., analyze signals from the sensors) and take appropriate action. In some examples, the appropriate action may comprise the processor 106 switching back to the low power mode of operation, because the signals analyzed were not indicative of the type of activity the sensor is intended to sense, for example. Lack of motion or other physical activity or lack thereof by user may serve to trigger entry into the low power mode of operation for processor 106. For example, sensor not detecting muscle activity may prompt processor 106 to switch to the low power mode of operation. Subsequently, detection of muscle activity may prompt processor 106 to exit the low power mode of operation. As another example, a motion sensor (e.g., an accelerometer, motion detector, or gyroscope) may output a signal indicative of no motion or motion below a threshold indicative of sufficient activity by user and that signal may prompt processor 106 to switch to the low power mode of operation. Subsequently, motion detector may generate a signal indicative of sufficient activity by user (e.g., running, walking, etc.) and processor 106 may switch out of the low power mode of operation to another mode where the signal from motion detector is analyzed and acted on.

Likewise, form-fitting sensor garment 102 (or more specifically controller 106 of form-fitting sensor garment 102) may automatically pair with the external display 170 or the headset 180 or the digital eyeglass 182 as described earlier. Likewise, SPCD 112 may automatically pair or otherwise establish a wireless communication link (e.g., via BT, WiFi, 2G, 3G, 4G, 5G, or other protocol) with one or more of the external display 170, the headset 180, or the digital eyeglass 182 as described above.

In an example, pairing may be assumed when two communication devices establish wireless communication (e.g., such as by the act of bringing the two devices closer together or by passing the devices over one another or tapping the devices together as in NFC or other low power close proximity RF protocol, or causing one device to communicate with another device). In one or more embodiments, the proposed pairing may be detected and optionally presented to the human subject (e.g., such as via a display screen 112a of SPCD 112) for approval by the human subject prior to the actual pairing. In this manner, pairing may be made automatic (e.g., with no user intervention) or substantially automatic (e.g., with minimal user intervention), greatly improving user friendliness aspect of the textile-based human MAF system 100.

In one or more embodiments, sensor data and/or analysis data may be time-stamped and automatically stored in one or more of controller 106, SPCD 112, and remote computer (198, 199) via Internet 120 in order to build up one or more user profiles over time, for example. This user profile data may be employed for historical analysis of workout sessions for a particular user, for customizing the system schema, for tracking workout progress, or for scientific/medical analysis by a third party, or for social/professional network sharing, and for challenges, for example. This aspect of automatic active management and updating the user profile presents a significant improvement over conventional workout data logging methods, which typically involve tediously manually writing down on paper or typing into an electronic device parameters regarding a workout session. Automatic paring and data logging make it more likely that the user would continue to use the textile-based human MAF system 100.

In accordance with an aspect of the present application, statistical correlations may be made over time to predict the weight that the human subject employs in a particular weight training exercise. Since data pertaining to the type of exercise and the equipment (obtained from the system schema at the stage 202) and pertaining to the user profile (e.g., body mass index (BMI), height, age, exercise history) is available, examples may correlate the weight employed (either input by the user initially via an appropriate input device or guessed by the system and confirmed or rejected by the human subject) with specific signature profile in the sensor signals. If a large set of such data is collected over time, statistical inferences may be made in the future to predict the weight being employed by the human subject even without an explicit input by the user pertaining to the weight employed. This statistical inference may be made based on, for example, the sensor signal amplitude or signature, the type of exercise and the equipment employed, the user profile, etc. Feedback by the human subject pertaining to weight prediction accuracy may be employed to refine the prediction model over time, thereby improving prediction accuracy as time goes by. Once weight prediction becomes more accurate and practical, record keeping may be further simplified since the user no longer has to manually enter the amount of weight used. Instant feedback and coaching may also become more meaningful when weight information is always accurately tracked and rendered available to the feedback/coaching logic.

In other examples, statistical correlation may also be made between sensor signals and exercise repetitions to automatically generate and log repetition data as the human subject exercises. Correlation can be made across multiple sensor signals to identify a particular workout or correlation on the signal itself to identify patterns representative or exercise repetitions. Likewise, statistical correlation may also be made between sensor signals and exercise duration to automatically generate and log duration data as the human subject exercises. Such duration data may be tracked with high granularity (e.g., time duration/repetition, time duration/set, time duration/exercise session, etc.) and with a high degree of consistency. Once repetition and duration information is automatically harvested, record keeping may be further simplified since the user no longer has to manually enter the repetition and duration information. Instant feedback and coaching may also become more meaningful when repetition and duration information is automatically tracked and rendered available to the feedback/coaching logic. Since information pertaining to the exercise involved and the exercise machine involved may also be automatically harvested and tracked, instant feedback, analysis, and coaching may be further enhanced.

As may be appreciated from the foregoing description, embodiments and exampled described herein may provide for a consumer-friendly system or platform for performing health-related and performance-related human monitoring, analyzing and feedback. By monitoring multiple muscles simultaneously and/or using multiple electromyography sensors and/or different types of sensors, and by leveraging technology widely adopted by consumers (e.g., the Internet, wireless interface, smart phones, etc.), the exercise data may be efficiently logged and the human subject may be given detailed and useful feedback and coaching pertaining not only to whether the muscle is being exercised, but also whether the right group of muscles are being exercised for a specific workout profile, whether a specific muscle is optimally exercised, whether the exercise form is correct, whether the pattern of muscle activation and/or intensity thereof indicates potential injury to one or more of the muscles in the relevant group, etc.

As may be appreciated from the foregoing description, embodiments and examples described herein may provide for a comprehensive and user-friendly textile-based human MAF system 100. By providing a plurality of sensors (e.g., 104A-104C or more) integrated on a compressive, form-fitting garment 102, problems associated with the aforementioned conventional gel-based and/or adhesive-based electrodes may be advantageously avoided. Since the sensors (e.g., 104A-104C or more) may monitor groups of muscles instead of an individual muscle, more sophisticated and useful analysis results (e.g., pertaining to form and injury monitoring) become possible. Calibration may help to improve data acquisition accuracy by taking into account different body types when acquiring data from the sensors (e.g., 104A-104C or more).

The use of different types of sensors together (e.g., a electromyography sensor and a bend-angle sensor and accelerometers) to monitor a human subject performance on a particular exercise routine greatly improves the accuracy and richness of the performance data acquired as well as improving the type of analysis and/or recommendation/coaching that can be provided. Real-time feedback and/or real time equipment alteration based on analysis result may also help optimize the exercise session and/or help reduce injury.

While the present application has been described in terms of several preferred embodiments and/or examples, there may be alterations, permutations, and equivalents, which fall within the scope of the present application. If the term "set" is employed herein, such term is intended to have its commonly understood mathematical meaning to cover zero, one, or more than one member. The present application should be understood to also encompass these alterations, permutations, and equivalents. It should also be noted that there are many alternative ways of implementing the systems, methods, computer readable media, and apparatuses of the present application. Although various examples are provided herein, it is intended that these examples be illustrative and not limiting with respect to the present application.

Although the foregoing examples have been described in some detail for purposes of clarity of understanding, the above-described concepts are not limited to the details provided. There are many alternative ways of implementing the above-described concepts for the present application. The disclosed embodiments and/or examples are illustrative and not restrictive.

What is claimed:

1. A method comprising:
   receiving a system schema for a plurality of muscles of a user, the system schema including a reference muscle activation data for each of the plurality of muscles;
   receiving signals from a set of sensors embedded into a garment such that the sensors make electrical contact with a skin surface of the user when the garment is worn by the user, wherein the received signals represent muscle activation data of the plurality of muscles acquired while the user performs an activity that exercises the plurality of muscles;
   comparing, for each muscle of a subset of the plurality of muscles, the acquired muscle activation data for the muscle to the reference muscle activation data for the muscle;
   generating feedback on the performance of the activity by the user based on the comparison; and
   modifying a display of a user device to include the generated feedback on the performance of the activity to the user.

2. The method of claim 1, wherein the generated feedback comprises audio including one or more of an exercise instruction, a form suggestion, or an injury warning.

3. The method of claim 1, wherein the generated feedback comprises a visual representation of a body of the user that is configured to depict the plurality of muscles being exercised.

4. The method of claim 3, wherein the visual representation of the body comprises an indication associated with each of the plurality of muscles, wherein the indication corresponds to one or more of the following: an intensity level, a duration, and a number of repetitions associated with each muscle.

5. The method of claim 1, wherein the generated feedback comprises a recommendation to the user about the performance of the activity, wherein the recommendation comprises one or more of an action and a movement associated with at least one of the plurality of muscles.

6. The method of claim 1, wherein the generated feedback is provided to the user during the performance of the activity or after the performance of the activity.

7. The method of claim 1, wherein the generated feedback is stored for playback at a future time.

8. The method of claim 1, wherein an exercise equipment is communicatively coupled to the garment and is configured to receive the acquired muscle activation data and automatically adjust one or more parameters of the exercise equipment based on the acquired muscle activation data.

9. The method of claim 1, wherein the feedback is generated by one or more of the garment, a controller coupled to the garment, or a mobile device communicatively coupled to the garment.

10. The method of claim 1, wherein at least some acquired muscle activation data corresponds to one of an exertion level of a muscle of the plurality of muscles.

11. The method of claim 1, further comprising displaying, by a mobile device of the user, the provided feedback, the mobile device wirelessly coupled to the garment.

12. The method of claim 1, wherein the set of sensors comprises less than all sensors embedded into the garment.

13. The method of claim 12, wherein the set of sensors is selected based on a type of the activity being performed by the user.

14. The method of claim 1, wherein the system schema and corresponding reference muscle activation data are determined based on one or more of previous usage of the garment by the user, demographic information of the user, information selected by the user, or information provided by a third party.

15. The method of claim 1, wherein the set of sensors embedded into the garment comprises redundant sensors.

16. A non-transitory computer-readable storage medium storing executable instructions that, when executed by a processor, perform steps comprising:
   receiving a system schema for a plurality of muscles of a user, the system schema including a reference muscle activation data for each of the plurality of muscles;
   receiving signals from a set of sensors embedded into a garment such that the sensors make electrical contact with a skin surface of the user when the garment is worn by the user, wherein the received signals represent muscle activation data of the plurality of muscles acquired while the user performs an activity that exercises the plurality of muscles;
   comparing, for each muscle of a subset of the plurality of muscles, the acquired muscle activation data for the muscle to the reference muscle activation data for the muscle;
   generating feedback on the performance of the activity by the user based on the comparison; and
   modifying a display of a user device to include the generated feedback on the performance of the activity to the user.

17. The non-transitory computer-readable storage medium of claim 16, wherein the generated feedback comprises audio including one or more of an exercise instruction, a form suggestion, or an injury warning.

18. The non-transitory computer-readable storage medium of claim 16, wherein the generated feedback comprises a visual representation of a body of the user that is configured to depict the plurality of muscles being exercised, wherein the visual representation of the body comprises an indication associated with each of the plurality of muscles, wherein the indication corresponds to one or more of the following: an intensity level, a duration, and a number of repetitions associated with each muscle.

19. The non-transitory computer-readable storage medium of claim 16, wherein the generated feedback comprises a recommendation to the user about the performance of the activity, wherein the recommendation comprises one or more of an action and a movement associated with at least one of the plurality of muscles.

20. The non-transitory computer-readable storage medium of claim 16, wherein the generated feedback is provided to the user during the performance of the activity or after the performance of the activity or is stored for playback at a future time.

21. The non-transitory computer-readable storage medium of claim 16, wherein an exercise equipment is communicatively coupled to the garment and is configured to receive the acquired muscle activation data and automatically adjust one or more parameters of the exercise equipment based on the acquired muscle activation data.

22. The non-transitory computer-readable storage medium of claim 16, wherein the set of sensors comprises less than all sensors embedded into the garment, and the set of sensors is selected based on a type of the activity being performed by the user.

* * * * *